(12) United States Patent
Li et al.

(10) Patent No.: US 10,391,109 B2
(45) Date of Patent: Aug. 27, 2019

(54) USE OF ZOLEDRONIC ACID TO PREPARE DRUG TREATING FATTY LIVER DISEASE

(71) Applicant: NANJING UNIVERSITY, Nanjing (CN)

(72) Inventors: Chaojun Li, Nanjing (CN); Bin Xue, Nanjing (CN); Shan Jiang, Nanjing (CN); Qiaoli Tang, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 15/740,817

(22) PCT Filed: Jun. 30, 2016

(86) PCT No.: PCT/CN2016/087963
§ 371 (c)(1),
(2) Date: Jan. 25, 2018

(87) PCT Pub. No.: WO2017/000902
PCT Pub. Date: Jan. 5, 2017

(65) Prior Publication Data
US 2018/0193364 A1    Jul. 12, 2018

(30) Foreign Application Priority Data

Jul. 1, 2015 (CN) .......................... 2015 1 0379220
Sep. 24, 2015 (CN) .......................... 2015 1 0617604

(51) Int. Cl.
*A61K 31/675* (2006.01)
*A61P 1/16* (2006.01)

(52) U.S. Cl.
CPC .............. *A61K 31/675* (2013.01); *A61P 1/16* (2018.01)

(58) Field of Classification Search
CPC .................................................. A61K 31/675
See application file for complete search history.

(56) References Cited

U.S. PATENT DOCUMENTS

2004/0202740 A1* 10/2004 Tan ..................... A61K 31/22
424/776
2013/0315981 A1* 11/2013 Ferrante, Jr. ......... A61K 31/675
424/450

FOREIGN PATENT DOCUMENTS

CN       1481247 A      3/2004
CN       105213407 A    1/2016

OTHER PUBLICATIONS

Adams et al., Treatment of non-alcoholic fatty liver disease, Postgraduate Medical Journal, 2006, vol. 82, Issue 967, 315-322.*
Wu, Ning et al. "Clinical Application Progress of Bisphosphonates", Chinise Journal of Misdiagnostics, vol. 7, No. 16, Aug. 31, 2007, pp. 3707-3709.
Kouichi Miura et. al, Hepatic recruitment of macrophages promotes nonalcoholic steatohepatitis through CCR2, the American Physiological Society, Mar. 22, 2012, G1310-G1321, 302.

* cited by examiner

*Primary Examiner* — Svetlana M Ivanova
(74) *Attorney, Agent, or Firm* — Gokalp Bayramoglu

(57) ABSTRACT

A method for treating fatty liver disease in a patient in need thereof, including a step of administering an effective amount of zoledronic acid. The fatty liver disease includes fatty liver disease caused by foodborne and hereditary factors, in particular non-alcoholic fatty liver. A dosage form of the zoledronic acid is an injection, a solution, a tablet, or a capsule.

5 Claims, 3 Drawing Sheets

USE OF ZOLEDRONIC ACID TO PREPARE DRUG TREATING FATTY LIVER DISEASE

CROSS REFERENCE TO RELATED APPLICATIONS

This application is the national phase entry of International Application No. PCT/CN2016/087963, filed on Jun. 30, 2016, which is based upon and claims priority to Chinese Patent Application No. CN201510379220.4, filed on Jul. 1, 2015, and Chinese Patent Application No. CN201510617604.5, filed on Sep. 24, 2015, the entire contents of which are incorporated herein by reference.

TECHNICAL FIELD

The present invention relates to a use of zoledronic acid, and in particular to a use of zoledronic acid in preparing a drug for treating fatty liver disease.

BACKGROUND

Fatty liver disease refers to a lesion with excessive accumulation of fat in liver cells caused by various reasons. Increased fat content in liver cells possibly results from fatty liver disease such as alcoholism, diabetes, hyperlipidemia, excess weight.

Non-alcoholic fatty liver disease (NAFLD) is a clinical pathophysiological syndrome characterized by steatosis of liver cells and lipid accumulation, caused by factors other than alcohols. Its broad spectrum includes pathological phases such as non-alcoholic fatty liver (NAFL), nonalcoholic steatohepatitis (NASH), liver fibrosis, and cirrhosis. The occurrence of this disease is mostly accompanied by increased body weight in patients. With the improvement of the economic level and the change of the life style, the incidence of non-alcoholic fatty liver disease is rising year by year and has become one of the most common chronic liver diseases.

The clinical manifestation of NAFLD varies with the causes, fat content and extent of inflammatory infiltration in liver, disease course, and concomitant underlying diseases such as obesity and diabetes. Most patients (48%-100%) have no symptoms of the liver disease, and a few patients may have nonspecific symptoms such as fatigue, discomfort in the right upper abdomen, or dull pain. Liver enlargement is the only sign in many patients, where the liver function exhibits slight impairment and the transaminase levels are elevated. Currently, it is considered that fatty liver mainly characterized by hepatic fat accumulation is benign, and may be ameliorated by the change of the life style, for example, adjusting the dietary habits and increasing the exercise. Thus, clinical treatment on non-alcoholic fatty liver is rarely reported, and there is no effective drug for clinical use in relieving fatty liver. For inadvertent or inadequate treatment, fatty liver in some patients can progress into irreversible liver diseases such as nonalcoholic steatohepatitis and liver fibrosis, and manifestations such as cirrhosis, jaundice, ascites, and gastrointestinal bleeding may eventually occur. With the occurrence of fatty liver disease, patients often exhibit different degrees of obesity, with a BMI out of limits and a waist-hip ratio out of limits.

Accumulation of liver triglyceride (TG) is reversible, and thus, drug-targeted reduction of TG in liver cells is of significant clinical importance for treatment of fatty liver disease, especially treatment and prevention of further progression of NAFLD.

In view of increased difficulty and high costs in the development of new drugs, the emphasis of drug development has shifted to secondary application of products, for example, expansion of new indications of developed drugs. Since an existing drug has been subjected to clinical trials and clinical observation in many cases for a long time, its safety can be more effectively ensured. Adverse reactions that occur can be appreciated more fully. For developing a new use of a clinical drug, the cost for clinical trials can be relatively reduced. Therefore, the research of a clinical drug to expand its new functions and indications can greatly promote the development of clinical treatment, save health resources, and facilitate the drug to realize its market values.

Zoledronic acid is described as follows: molecular formula: $C_5H_{10}N_2O_7P_2$; chemical name: 1-hydroxy-2-(imidazol-1-yl)-ethylidene-1,1-bisphosphonic acid; zoledronic acid; chemical structure represented by formula I:

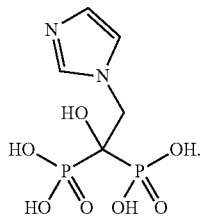

Formula I

At present, zoledronic acid has been widely used clinically for treating metabolic bone diseases such as osteoporosis, osteitis deformans, and cancerous bone metastasis. Zoledronic acid has a significant inhibition effect on bone resorption. Zoledronic acid and also alendronate sodium and risedronate sodium are third-generation bisphosphonate drugs, which are different from first-generation nitrogen-free bisphosphonates such as etidronate sodium and clodronate sodium and second-generation nitrogen-containing bisphosphonates such as pamidronate sodium and tiludronate sodium in that the third-generation bisphosphonate drugs have the strongest bone resorption resistance with less toxic side effects. The primary molecular structure of zoledronic acid comprises a P-C-P group as active group and R1 and R2 groups as pendent substituents. These primary groups determine the biological activity and mechanism of action of zoledronic acid. Clinically, zoledronic acid is mainly targeted to osteoclasts, for example, by blocking bone destruction and resorption by osteoclasts, interfering with the growth of osteoclasts, and inducing the apoptosis of osteoclasts. In addition, zoledronic acid can also be directly targeted to a key enzyme of the mevalonate/isoprenoid pathway in osteoclasts—farnesyl pyrophosphate synthase (FPPS), so that the formation of isoprenoid compounds such as farnesyl pyrophosphate (FPP) and geranylgeranyl pyrophosphate (GGPP) is reduced, and thus several signaling pathways in which GTPases are involved are blocked. However, the use of zoledronic acid in treating fatty liver disease has not been reported.

SUMMARY

In view of this, an object of the present invention is to determine whether zoledronic acid can be used as a drug for treating fatty liver disease by investigating the conditions in mice with foodborne and hereditary lipid accumulation in liver after injection of zoledronic acid, thereby opening a new way for treating fatty liver disease and providing a new indication of zoledronic acid in clinical applications.

A primary mode of administration of zoledronic acid used in the present invention is clinically intravenous infusion, where a drug from intravenous injection will enter the systemic circulation and mainly acts on other organs. Animals are dosed through the tail vein, and similar to clinical oral administration, the primary organ for metabolism is the liver, so that the loss of the drug due to its first delivery to other organs and then return to the liver can be reduced. In the function for treating fatty liver disease such as non-alcoholic fatty liver, the mode of drug administration may also be oral administration, liver specific administration or systemic administration (for example, by penetrating the skin, by nasal inhalation, or using suppositories). Zoledronic acid of the present invention may also be prepared into injections, for example, by a conventional method with a physiological salt solution or an aqueous solution containing glucose and other adjuvants. Drugs such as tablet and capsule may be prepared by a conventional method. Injection, solution, tablet, and capsule are advantageously prepared under sterile conditions.

The present invention provides a use of zoledronic acid in preparing a drug for treating liver disease, the liver disease comprising fatty liver disease.

Preferably, the fatty liver disease comprises fatty liver disease caused by foodborne and hereditary factors.

Preferably, the fatty liver disease is non-alcoholic fatty liver or hepatic function injury.

Preferably, the dosage form of zoledronic acid is injection, solution, tablet, or capsule.

Preferably, the dosage of zoledronic acid is 50 µg/kg or 200 µg/kg per injection, once every two days.

The present invention proposes a use of zoledronic acid in preparing a drug for treating liver disease, the liver disease comprising fatty liver disease and hepatic function injury, the fatty liver disease comprising fatty liver disease caused by foodborne and hereditary factors, especially non-alcoholic fatty liver. According to the present invention, zoledronic acid can be used to effectively treat liver disease, slow hepatic lipid accumulation and steatosis, significantly slow non-alcoholic fatty liver, reduce blood alanine transaminase and aspartate transaminase levels, and reduce the body weight, thereby opening a new way for treating fatty liver disease and hepatic function injury, providing a new indication of zoledronic acid in clinical applications, and opening a potentially promising prospect of zoledronic acid in the treatment area of liver diseases. In addition, zoledronic acid has been applied in clinically treating metabolic bone diseases, with fewer side effects and lower costs relative to the development of new drugs.

DETAILED DESCRIPTION OF THE INVENTION

Figure 1:
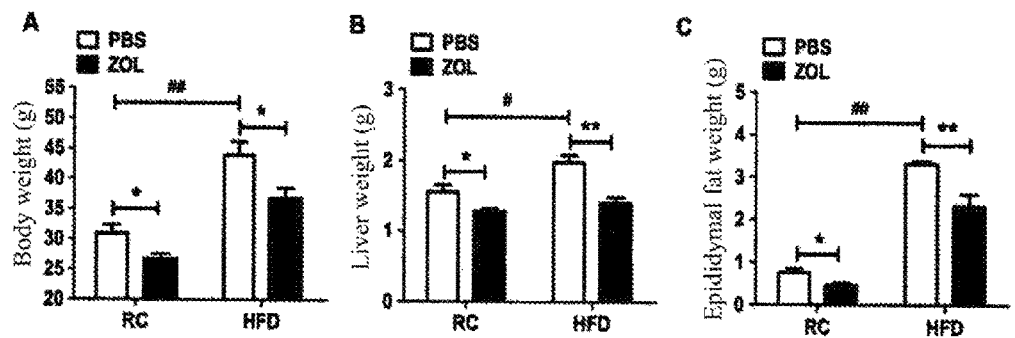
FIG. 1 shows the changes of body weight and primary organ for lipid metabolism in mice after administration of zoledronic acid.

The present invention is further described in detail below with reference to the accompanying drawings and examples.

The following examples are only used for illustrating the present invention and are not intended to limit the scope of the present invention. Experimental methods in the examples where specific conditions are not indicated usually use conventional conditions, for example, those described in Molecular Cloning: A Laboratory Manual, or use those recommended by manufacturers.

General Materials and Methods

Materials:

8-week-old C57BL/6J mice and 10-week-old ob/ob mice were purchased from Model Animal Research Center of Nanjing University. Regular chow for mice was purchased from Jiangsu XIETONG Bioengineering Co., Ltd. High-fat diet was purchased from Research Diets, New Brunswick, N.J. Zoledronic acid was purchased from Novartis Pharma Schweiz AG. Oil Red dye was purchased from SIGMA-ALDRICH (China). Tissue TG assay kit was purchased from Plant Bioengineering Co., Ltd.

Method 1 Measurement of TG in Liver Tissue

About 50 mg of the right lobe of liver in mice was taken, with an accurate weight recorded. It was washed with PBS, placed in 1 ml of a lysis solution and mechanically homogenized. The lysed tissue homogenate was divided into two portions. One portion, 500 µl, was placed in a metal bath at 70° C., heated for 10 min, and centrifuged for 5 min at 2,000×rpm. 1-10 µl was taken for a tissue TG assay with the kit. Another 500 µl was used for a protein concentration assay using the BCA method.

Method 2 Preparation of Paraffin Sections

An appropriate amount of the right lobe of liver tissue was taken, fixed in 4% paraformaldehyde for 24-48 h, dehydrated with graded ethanols, cleared with xylene, infiltrated with wax, embedded in paraffin, and sectioned at a thickness of 5 µm.

Method 3 H&E Staining of Paraffin Sections

The sections were de-waxed in xylene for 10 min and 5 min respectively, and then reconstituted in graded ethanol solutions. The sections were subjected to hematoxylin staining for 4 min, and then slightly washed with distilled water. The sections were blued in 0.25% $NH_3.H_2O$ for 30 s, and then washed with distilled water. The sections were dehydrated with graded ethanols to 95% ethanol, stained for 2-3 s in 0.5% eosin, dehydrated in 100% ethanol, and soaked in xylene for 2 min. Finally, the sections were mounted in Rhamsan gum.

Method 4 Preparation of Cryosections

An appropriate amount of the right lobe of liver was taken at the same site for laboratory mice in each group, fixed in paraformaldehyde for 2 h, dehyrdated with 30% sucrose for 8-12 h, and embedded in OCT. It was stored in a refrigerator at −70° C. It was sectioned using a Cryostat Microtome at a section thickness of 15 μm.

Method 5 Oil Red Staining

The cryosections were slightly dried at room temperature, slightly washed with 60% ethanol, stained in an Oil Red 0 staining solution (60% Oil Red 0 stock plus 40% distilled water) for 10-15 min, differentiated in 60% ethanol, washed, subjected to nuclear staining with hematoxylin for 1 min, washed for 1 min, suck dried, and mounted with glycerin.

Method 6 Assay for ALT and AST Levels

After the mice were anaesthetized, blood was collected from the eye socket veins, left at room temperature for 30 min, and centrifuged upon serum precipitation. 10 μl serum was taken for ALT and AST assays with the kit.

The present inventors first used model mice with food-borne non-alcoholic fatty liver, that is, high-fat diet (containing 60% fat) was used for inducing C57BL/6J mice for 12 weeks to generate fatty liver. It was found from the experimental assay that feeding of high fat diet could result in hepatic fat accumulation and degeneration in mice.

Establishment and Grouping of Non-Alcoholic Fatty Liver Mouse Models

A total of forty 8-week-old C57BL/6J mice were selected, and randomly assigned to 4 groups of 10 mice. The mice were weighted respectively, fed with regular chow (containing 4% fat) and high fat diet (containing 60% fat), and housed for 12 weeks. The mice were weekly weighted and recorded, and curves were plotted. After 12 weeks, the mice with fatty liver fed with regular chow and high fat diet were administered with zoledronic acid and placebo so as to explore the function for relieving fat accumulation. Meanwhile, the resulting changes of physiological indicators for mice were observed, and different body weights and physiological indicators were recorded. The data is shown in Table 1.

TABLE 1

Body weights and physiological indicators for mice after administration

| Experimental group | | Average body weight/g | Average liver weight/g | Average epididymal fat pad weight/g |
|---|---|---|---|---|
| RC group | PBS | 30.88 ± 3.32 | 1.55 ± 0.22 | 0.76 ± 0.18 |
| | ZOL | 26.72 ± 1.69 | 1.28 ± 0.08 | 0.46 ± 0.11 |
| | Average decline | 13% | 17% | 39% |
| HFD group | PBS | 43.88 ± 5.08 | 1.98 ± 0.22 | 3.33 ± 0.16 |
| | ZOL | 36.73 ± 3.74 | 1.41 ± 0.17 | 2.33 ± 0.62 |
| | Average decline | 16% | 29% | 30% |

The RC group is regular chow group, the HFD group is high fat diet group, PBS is placebo, ZOL is zoledronic acid, and the dosage is 50 μg/kg.

It can be known from Table 1 that after administration of ZOL, the mice in the HFD and RC groups all show significant decreases in body weight, and also significant decreases in liver weight and epididymal fat pad weight. In the RC group, the average body weight with administration of ZOL is decreased compared to that with administration of PBS by 13%; in the HFD group, the average body weight with administration of ZOL is decreased compared to that with administration of PBS by 16%. It can be seen that administration of ZOL can significantly decrease the body weight, and administration of ZOL has a more significant effect in decreasing the body weight and results in more decrease in lipid accumulation for the HFD group than for the RC group. In the RC group, the average liver weight with administration of ZOL is decreased compared to that with administration of PBS by 17%; in the HFD group, the average liver weight with administration of ZOL is decreased compared to that with administration of PBS by 29%. It can be seen that administration of ZOL can significantly decrease the liver weight, and administration of ZOL has a more significant effect for the HFD group than for the RC group. In the RC group, the average epididymal fat pad weight with administration of ZOL is decreased compared to that with administration of PBS by 39%; in the HFD group, the average epididymal fat pad weight with administration of ZOL is decreased compared to that with administration of PBS by 30%. It can be seen that administration of ZOL can significantly decrease the epididymal fat pad weight.

FIG. 1 shows the changes of body weight and primary organ for lipid metabolism in mice after administration of zoledronic acid. * and # indicate that there is a statistically significant difference when both are compared, and ** and ## indicate that there is a very significant statistical difference. FIG. 1A shows a significant decrease in body weight; FIG. 1B shows a significant decrease in liver weight; and FIG. 1C shows a significant decrease in epididymal fat pad weight. Thus, it can be seen that treatment with zoledronic acid can significantly inhibit increase in body weight in mice caused by high fat diet, indicating that zoledronic acid can significantly improve increase in body weight in obese mice. It is found in the assay that the epididymal fat pad weight in mice is significantly decreased, indicating that zoledronic acid can inhibit fat production, and has strong weight loss effect in terms of decreasing fat accumulation and facilitating body weight reduction in an individual.

Example 1 Effect of Zoledronic Acid on Foodborne Non-Alcoholic Fatty Liver

For a patient with fatty liver clinically, the liver exhibits swelling in appearance, and this is mainly due to lipid accumulation. This lipid accumulation can be observed by obtaining the liver tissue by needle biopsy and by H&E staining and Oil Red staining. Therefore, this direct assay with H&E and Oil Red is a better method for observing lipid accumulation.

Figure 2:
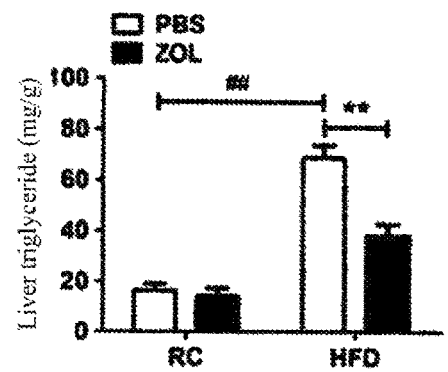
FIG. 2 is a bar graph showing the changes of hepatic lipid content in mice after administration of zoledronic acid.
Figure 3:
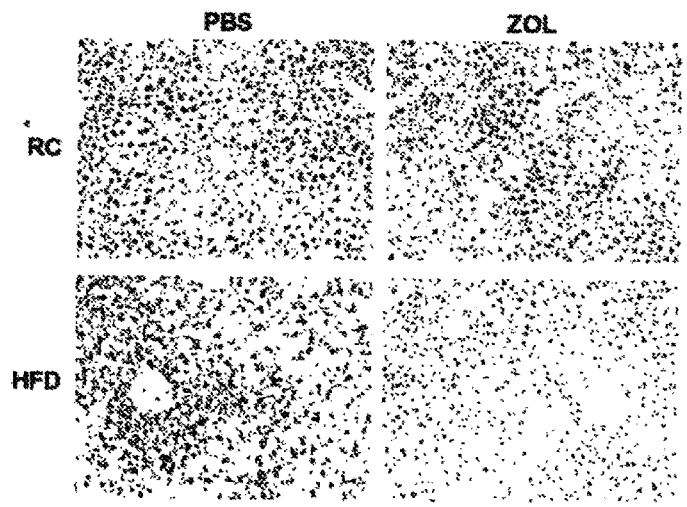
FIG. 3 shows optical micrographs after paraffin sectioning and H&E staining of the liver in mice after administration of zoledronic acid.

According to the forgoing general materials and methods, the mice in the HFD group were first administered with zoledronic acid and placebo. In this example, zoledronic acid was administered mainly by tail vein injection. The primary site of action of the drug was liver. The injection was performed once every two days. The dosage was 50 μg/kg of zoledronic acid. Tissue triglyceride level assay and H&E staining were performed for mice after administration. The experimental data is shown in Table 2, and the results are shown in FIG. 2 and FIG. 3.

TABLE 2

Liver triglyceride content in mice after administration

| Experimental group | | Liver triglyceride mg/g |
|---|---|---|
| RC group | PBS | 16.38 ± 5.53 |
| | ZOL | 14.33 ± 6.39 |
| | Average decline | 12.5% |

TABLE 2-continued

Liver triglyceride content in mice after administration

| Experimental group | | Liver triglyceride mg/g |
|---|---|---|
| HFD group | PBS | 68.85 ± 11.26 |
| | ZOL | 38.18 ± 10.27 |
| | Average decline | 44.9% |

The HFD group is high fat diet group, the RC group is regular chow group, PBS is placebo, ZOL is zoledronic acid, and the dosage is 50 μg/kg.

It can be known from Table 2 that a significant decrease in liver triglyceride occurs in mice for the HFD and RC groups after administration of ZOL. In the RC group, liver triglyceride with administration of ZOL is decreased compared to that with administration of PBS by 12.5%; in the HFD group, liver triglyceride with administration of ZOL is significantly decreased compared to that with administration of PBS by 44.9%. It can be seen that administration of ZOL can significantly reduce liver triglyceride.

FIG. 2 shows the changes of liver triglyceride content in mice after administration of zoledronic acid, where the hepatic lipid content is quantitatively analyzed. ** and ## indicate that there is a very significant statistical difference. It can be known from the experimental results that the induction with high fat diet may result in increase in TG accumulation. The TG content is increased in the placebo group, while the TG content is decreased in the zoledronic acid group, indicating that after injection of zoledronic acid, hepatic lipid accumulation is significantly decreased. Thus, it can be known that the zoledronic acid preparation can effectively decrease foodborne lipid accumulation in liver and effectively treat foodborne non-alcoholic fatty liver. FIG. 3 shows optical micrographs after paraffin sectioning and H&E staining of the liver in mice after administration of zoledronic acid, showing that after injection of zoledronic acid, there is a significant remission in hepatic macrovesicular steatosis, that is, hepatic lipid degeneration induced by high fat diet is reduced. Adult-onset obesity is divided into central obesity and peripheral obesity. It may also be divided into subcutaneous fat type obesity and visceral obesity according to different lipid accumulation sites. Increase of visceral fat often results in the development of cardiovascular disease and insulin resistance. The zoledronic acid preparation of the present invention can effectively inhibit lipid accumulation in liver, reduce triglyceride content in body, relieve hepatic steatosis, effectively and specifically reduce visceral fat accumulation in an individual, and predictably reduce the probability of occurrence of cardiovascular disease in a patient.

Example 2 Effect of Zoledronic Acid on Foodborne Fatty Hepatic Function Injury

Figure 4:
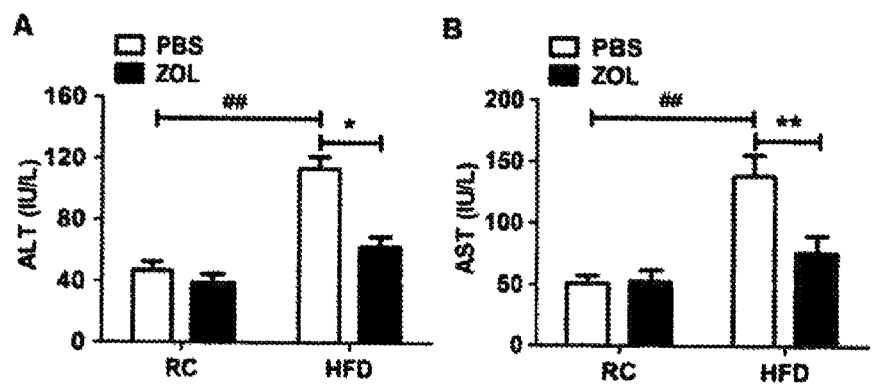
FIG. 4 shows the changes of blood alanine transaminase and aspartate transaminase contents in mice after administration of zoledronic acid.

Similar to Example 1, according to the forgoing general materials and methods, the mice in the HFD group were first administered with zoledronic acid and placebo. The blood alanine transaminase (ALT) and aspartate transaminase (AST) levels in mice after administration were assayed. The experimental data is shown in Table 3, and the results are shown in FIG. 4A and FIG. 4B.

TABLE 3

Blood alanine transaminase (ALT) and aspartate transaminase (AST) levels in mice after administration.

| Experimental group | | ALT IU/L | AST IU/L |
|---|---|---|---|
| RC group | PBS | 47 ± 12.51 | 50.8 ± 14.34 |
| | ZOL | 39.2 ± 12.09 | 52.4 ± 21.20 |
| | Average decline | No significant change | No significant change |
| HFD group | PBS | 113.6 ± 17.10 | 138.6 ± 38.82 |
| | ZOL | 62.8 ± 14.08 | 76 ± 31.42 |
| | Average decline | 44.7% | 45.2% |

The HFD group is high fat diet group, the RC group is regular chow group, PBS is placebo, ZOL is zoledronic acid, and the dosage is 50 μg/kg.

It can be known from Table 3 that for the HFD group, the ALT and AST levels are significantly decreased after administration of ZOL. In the RC group, there are no significant changes in ALT and AST with administration of ZOL compared to administration of PBS. The values measured in the RC group are in a normal range, and administration of ZOL does not affect the hepatic function. In the HFD group, the AST level is decreased with administration of ZOL compared to administration of PBS by 44.7%, and the ALT level is decreased by 45.2%. It can be seen that administration of ZOL can significantly reduce the ALT and AST levels in mice, thereby relieving the hepatic injury.

FIG. 4A shows the changes of blood alanine transaminase content in mice after administration of zoledronic acid, and FIG. 4B shows the changes of blood aspartate transaminase content in mice after administration of zoledronic acid. * indicates that there is a statistically significant difference when both are compared, and ** and ## indicate that there is a very significant statistical difference. The results show that after injection of zoledronic acid, ALT and AST levels in mice are reduced by zoledronic acid, indicating that zoledronic acid can effectively antagonize the damage of liver function by hepatic fat accumulation. Fatty liver disease may lead to the liver injury because excessively increased triglyceride initiates various forms of inflammation, which in turn acts on hepatocytes resulting in necrosis of liver cells, thereby damaging the liver function. Zoledronic acid can effectively reduce triglyceride content in body, thereby reducing inflammatory response in liver and improving hepatic function injury. Therefore, zoledronic acid can protect the human liver by modulating lipid accumulation, achieving the effect of liver protection.

Example 3 Effect of Zoledronic Acid on Hereditary Non-Alcoholic Fatty Liver

Figure 5:
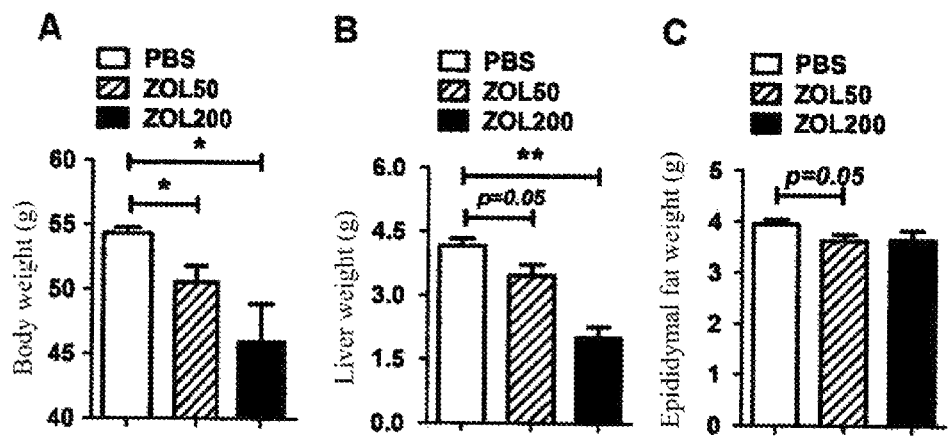
FIG. 5 shows the changes of body weight and primary organ for lipid metabolism in ob/ob mice after administration of zoledronic acid at various dosages.

In order to further verify the lipid reducing effect of zoledronic acid, the experiments of the present invention were carried out in ob/ob mice of hereditary obese mice models with severe non-alcoholic fatty liver mainly characterized by lipid accumulation. A total of thirty 10-week-old ob/ob mice were selected, randomly assigned to 3 groups of 10 mice, and housed with regular chow (containing 4% fat). Ob/ob mice were mutant mice mainly manifested as obesity and related metabolic syndrome. The liver of ob/ob mice exhibited significant steatosis. Ob/ob mice were administered with zoledronic acid and control placebo. The resulting changes of physiological indicators in mice were observed and different body weights and physiological indicators were recorded. The data is shown in Table 4, and the results are shown in FIG. 5.

TABLE 4

Body weights and physiological indicators for ob/ob mice after administration

| Experimental group | | Average body weight/g | Average liver weight/g | Average epididymal fat pad weight/g |
|---|---|---|---|---|
| Ob/ob mice | PBS | 54.34 ± 0.88 | 4.16 ± 0.38 | 3.95 ± 0.20 |
| | ZOL50 | 50.56 ± 2.82 | 3.47 ± 0.58 | 3.628 ± 0.27 |
| | Average decline | 7% | 17% | 39% |
| | ZOL200 | 45.94 ± 5.16 | 2.26 ± 0.21 | 3.79 ± 0.30 |
| | Average decline | 15% | 46% | 4% |

PBS is placebo, ZOL50 indicates that the dosage of zoledronic acid is 50 μg/kg, and ZOL200 indicates that the dosage of zoledronic acid is 200 μg/kg.

It can be known from Table 4 that the ob/ob mice all show significant decreases in body weight, and also significant decreases in liver weight and epididymal fat pad weight. Compared to administration of PBS, administration of ZOL50 and administration of ZOL200 result in decreases in average body weight of 7% and 15% respectively, decreases in average liver weight of 17% and 46% respectively, and decreases in average epididymal fat pad weight of 39% and 4% respectively.

FIG. 5 shows the changes of body weight and primary organ for lipid metabolism in ob/ob mice after administration of zoledronic acid at various dosages. FIG. 5A shows significant decreases in body weight after administrations of ZOL50 and ZOL200, FIG. 5B shows significant decreases in liver weight after administrations of ZOL50 and ZOL200, and FIG. 5C shows partial decreases in epididymal fat pad weight after administrations of ZOL50 and ZOL200. * indicates that there is a statistically significant difference when both are compared, and ** indicates that there is a very significant statistical difference.

Liver triglyceride and lipid contents were further quantitatively analyzed, as shown in Table 5.

TABLE 5

Liver triglyceride and lipid contents in ob/ob mice after administration of zoledronic acid at various dosages.

| Experimental group | | Liver triglyceride mg/g | Lipid content mg/ml |
|---|---|---|---|
| Ob/ob mice | PBS | 149.14 ± 10.53 | 743.98 ± 48.49 |
| | ZOL50 | 140.88 ± 44.29 | 592.00 ± 201.08 |
| | Average decline | No significant change | 20.4% |
| | ZOL200 | 98.49 ± 40.08 | 490.22 ± 211.95 |
| | Average decline | 34% | 34% |

It can be known from Table 5 that compared to the PBS administration group, after administration of ZOL50, there is no significant change in liver triglyceride for ob/ob mice, and the decline in lipid content is 20.4%, which shows a significant decrease; and after administration of ZOL200, the changes of liver triglyceride and lipid contents both are 34%, which show very significant decreases, indicating that ZOL can result in a significant decrease in hepatic lipid accumulation.

Figure 6:
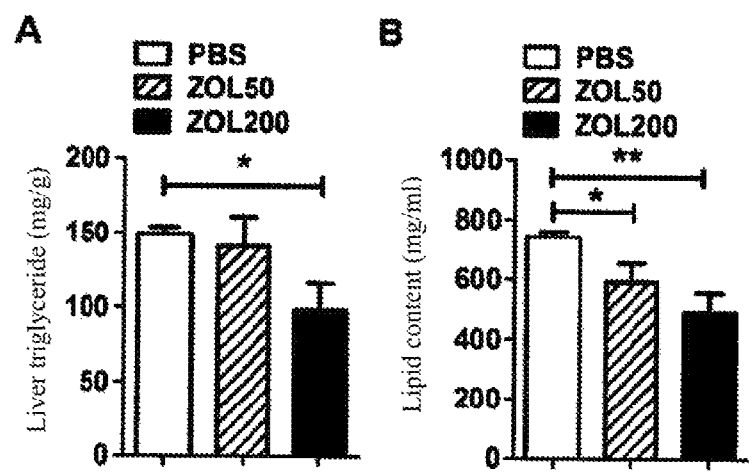
FIG. 6 shows the changes of hepatic lipid content in ob/ob mice after administration of zoledronic acid at various dosages.

FIG. 6 shows the changes of hepatic lipid content. FIG. 6A shows quantitative analysis of hepatic lipid content; and FIG. 6B shows quantitative analysis of hepatic lipid content in mice by Computer Tomography (CT), indicating that after injection of zoledronic acid, hepatic lipid accumulation is significantly decreased.  indicates that there is a statistically significant difference when both are compared, and  indicates that there is a very significant statistical difference.

Figure 7:
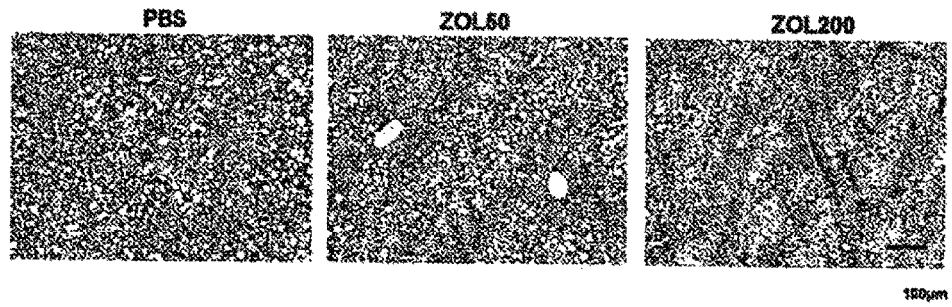
FIG. 7 shows optical micrographs after paraffin sectioning and H&E staining of the liver in ob/ob mice after administration of zoledronic acid at various dosages.
Figure 8:
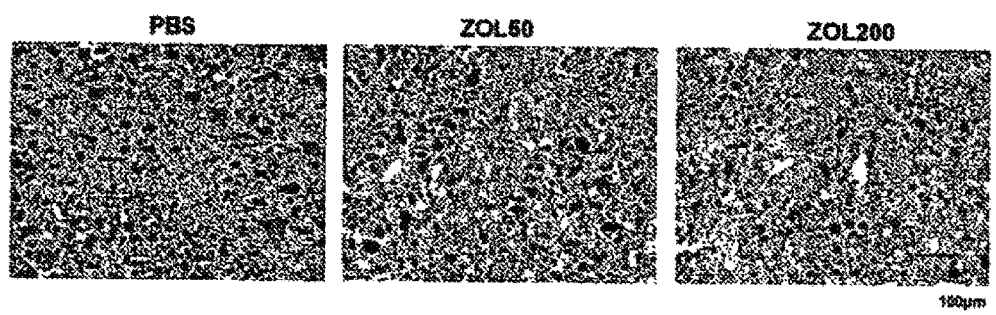
FIG. 8 shows optical micrographs after cryosectioning and Oil Red staining of the liver in ob/ob mice after administration of zoledronic acid at various dosages.

Further, the liver structure was shown by H&E staining and the lipid accumulation was shown by Oil Red staining. Injection of zoledronic acid can effectively reduce hepatic lipid accumulation in hereditary obese mice. FIG. 7 shows optical micrographs after paraffin sectioning and H&E staining of the liver in ob/ob mice after administration of zoledronic acid at various dosages, showing that after injection of zoledronic acid, there is a significant decrease in hepatic lipid accumulation, and hepatic lipid degeneration is relieved. FIG. 8 shows optical micrographs after cryosectioning and Oil Red staining of the liver in ob/ob mice after administration of zoledronic acid at various dosages, showing that after injection of zoledronic acid, there is a significant decrease in hepatic lipid accumulation, and hepatic steatosis is relieved. The above results indicate that the zoledronic acid preparation can effectively reduce hepatic lipid accumulation in hereditary obese mice, and can effectively treat hereditary non-alcoholic fatty liver. In addition, the use of the zoledronic acid preparation can effectively reduce the body weight of hereditary obese mice, effectively reduce accumulation of epididymal fat pads in mice, and modulate the triglyceride content in body, achieving an effective lipid reducing, lipid lowering, and slimming effect.

Example 4 Effect of Zoledronic Acid on Hereditary Fatty Hepatic Function Injury

Figure 9:
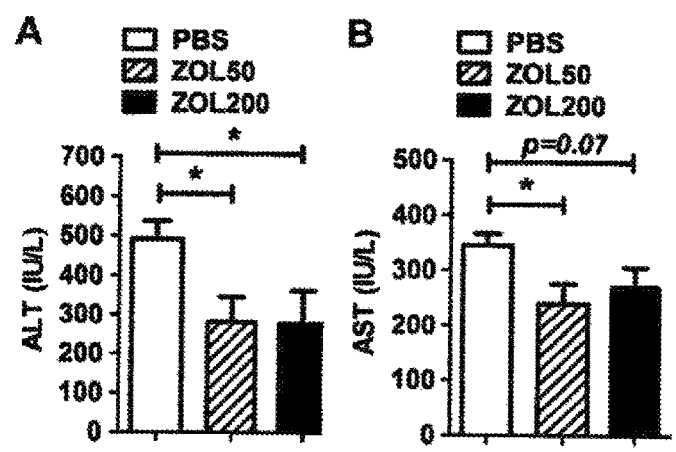
FIG. 9 shows the changes of blood alanine transaminase and aspartate transaminase contents in ob/ob mice after administration of zoledronic acid at various dosages.

Similar to Example 1, according to the forgoing general materials and methods, ob/ob mice were first administered with zoledronic acid preparation and placebo at various dosages. The blood ALT and AST levels in ob/ob mice after treatment were assayed. The data is shown in Table 6, and the results are shown in FIG. 9A and FIG. 9B.

TABLE 6

Blood ALT and AST levels in ob/ob mice

| Experimental group | | ALT IU/L | AST IU/L |
|---|---|---|---|
| Ob/ob mice | PBS | 490.2 ± 100.25 | 345.2 ± 46.66 |
| | ZOL50 | 281.6 ± 142.59 | 240.25 ± 70.54 |
| | Average decline | 42.5% | 30.4% |
| | ZOL200 | 277.4 ± 188.65 | 269.75 ± 71.53 |
| | Average decline | 43.4% | 21.9% |

It can be known from Table 6 that after administration of ZOL50, the averages of ALT and AST levels in mice are decreased by 42.5% and 30.4% respectively, which show significant decreases; and after administration of ZOL200, the averages of ALT and AST levels are decreased by 43.4% and 21.9% respectively. However, P value is 0.07 when the ALT level decrease is compared to that in the PBS administration group, showing a non-significant change. Nevertheless, it can still be indicated that ZOL can result in partial decreases in ALT and AST levels.

FIG. 9A shows the change of blood alanine transaminase content in ob/ob mice after administration of zoledronic acid at various dosages; and FIG. 9B shows the change of blood aspartate transaminase content in ob/ob mice after administration of zoledronic acid at various dosages. Blood ALT and AST assays show that administration of zoledronic acid reduces blood transaminase levels, and reduces ALT and AST levels in hereditary obese mice, indicating that the zoledronic acid preparation can protect against the damage of liver function, thereby protecting the liver function.

According to the present invention, zoledronic acid can effectively reduce hepatic lipid accumulation caused by foodborne and hereditary factors, has a significant effect in relieving non-alcoholic fatty liver, and can effectively prevent and/or treat non-alcoholic fatty liver. Zoledronic acid can reduce ALT and AST levels in foodborne and hereditary obese mice, indicating that the zoledronic acid preparation can protect against the damage of liver function caused by hereditary obesity, achieving liver protection effect. Zoledronic acid provides a new way and means for a wide range of patients with hereditary obesity. Zoledronic acid can also effectively function to protect the liver while effectively reducing the fat and achieving the slimming effect, and this effect would be significantly distinct from toxic liver damage with use of other drugs.

What is claimed is:

1. A method of treating fatty liver disease in a human, comprising administering zoledronic acid to treat the fatty liver disease; wherein a dosage range of the zoledronic acid is from 50 µg/kg to 200 µg/kg per intravenous injection, once every two days.

2. The method according to claim 1, wherein the fatty liver disease comprises fatty liver disease caused by foodborne and hereditary factors.

3. The method according to claim 1, wherein the fatty liver disease is non-alcoholic fatty liver or hepatic function injury.

4. The method according to claim 1, wherein a drug administration of the zoledronic acid comprises liver-specific and systemic administration.

5. The method according to claim 1, wherein the dosage of zoledronic acid is 50 µg/kg or 200 µg/kg.

* * * * *